United States Patent
Fang et al.

(10) Patent No.: US 12,129,219 B2
(45) Date of Patent: Oct. 29, 2024

(54) CALCIUM-BASED CATALYST AND METHOD FOR CATALYTICALLY SYNTHESIZING ALKANOLAMIDE SURFACTANT THEREOF

(71) Applicant: Jiangnan University, Wuxi (CN)

(72) Inventors: Yun Fang, Wuxi (CN); Xueyi Hu, Wuxi (CN); Yongmei Xia, Wuxi (CN)

(73) Assignee: Jiangnan University, Wuxi (CN)

( * ) Notice: Subject to any disclaimer, the term of this patent is extended or adjusted under 35 U.S.C. 154(b) by 978 days.

(21) Appl. No.: 17/113,343

(22) Filed: Dec. 7, 2020

(65) Prior Publication Data

US 2021/0087136 A1    Mar. 25, 2021

Related U.S. Application Data

(63) Continuation of application No. PCT/CN2020/082079, filed on Mar. 30, 2020.

(30) Foreign Application Priority Data

May 31, 2019  (CN) .......................... 201910469860.2

(51) Int. Cl.
*C07C 231/02* (2006.01)
*B01J 23/04* (2006.01)
(Continued)

(52) U.S. Cl.
CPC ............. *C07C 231/02* (2013.01); *B01J 23/04* (2013.01); *B01J 37/0236* (2013.01);
(Continued)

(58) Field of Classification Search
None
See application file for complete search history.

(56) References Cited

FOREIGN PATENT DOCUMENTS

| CN | 1427816 A | 7/2003 |
|---|---|---|
| CN | 101774936 A | 7/2010 |

(Continued)

OTHER PUBLICATIONS

Kumar ("One-pot solvent-free synthesis of fatty acid alkanoamides from natural oil triglycerides using alkali metal doped CaO nanoparticles as heterogeneous catalyst" Journal of Industrial and Engineering Chemistry 38 (2016) p. 43-49, including Supporting Information (SI) p. S1-S6). (Year: 2016).*

(Continued)

*Primary Examiner* — Amy C Bonaparte
(74) *Attorney, Agent, or Firm* — IPRO, PLLC (57) ABSTRACT

Provided is a calcium-based catalyst and a method for catalytically synthesizing an alkanolamide surfactant thereof. The method includes the preparation of the catalyst, and then catalyzing a reaction of fat and oil, or fatty acid ester and alkanolamine with the catalyst to synthesize a light colored alkanolamide surfactant with less free alkanolamine. The catalyst has a slow release feature, so that late in the reaction, the catalyst still has relatively high catalytic reactivity, guaranteeing a high conversion rate of the alkanolamine into the alkanolamide surfactant, the, product residual quantity of alkanolamine is low, while the risk of nitrosamine production due to product residual alkanolamine is greatly lowered. Due to catalyst slow release control, the early reaction period speed is greatly reduced, thereby avoiding a deepened product color caused by poor heat transfer due to an early reaction period being excessively fast.

15 Claims, 1 Drawing Sheet

(51) Int. Cl.
  *B01J 37/02*   (2006.01)
  *B01J 37/03*   (2006.01)
  *B01J 37/04*   (2006.01)
  *C09K 23/22*   (2022.01)

(52) U.S. Cl.
  CPC ............. *B01J 37/038* (2013.01); *B01J 37/04* (2013.01); *C09K 23/22* (2022.01)

(56) References Cited

FOREIGN PATENT DOCUMENTS

| | | | | |
|---|---|---|---|---|
| CN | 104140792 A | * | 11/2014 | ............... C09K 8/32 |
| CN | 105439881 A | | 3/2016 | |
| CN | 107556208 A | | 1/2018 | |
| CN | 110152645 A | | 8/2019 | |
| JP | 2013199438 A | | 10/2013 | |

OTHER PUBLICATIONS

Dinesh Kumar, One step synthesis of fatty acid diethanolamides and methyl esters from triglycerides using sodium doped calcium hydroxide as a nanocrystalline heterogeneous catalyst, New Journal of Chemistry, vol. 9, Issue 39, Jul. 1, 2015, p. 7097-7104.

* cited by examiner

CALCIUM-BASED CATALYST AND METHOD FOR CATALYTICALLY SYNTHESIZING ALKANOLAMIDE SURFACTANT THEREOF

TECHNICAL FIELD

The present disclosure relates to a calcium-based catalyst and a method for catalytically synthesizing an alkanolamide surfactant thereof, and belongs to the technical field of surfactant synthesis.

BACKGROUND

Alkanolamide is a nonionic surfactant with excellent properties such as thickening, foam stabilizing and emulsifying, is often used as a thickening and foam-stabilizing assistant for liquid wash supplies, and is also used as a fat liquoring assistant for textile products, an anti-rust assistant for cleaning and corrosion resistance of metal surfaces and a lubricant for a machining process and the like.

According to raw material sources of long-chain acyl donors, methods for synthesizing an alkanolamide surfactant mainly include a fatty acid method, a fatty acid low carbon alcohol ester method and a fat and oil method. In 1937, Wolf Kritchevsky first developed synthesis of alkanolamide through reaction of fatty acids and diethanol amine, but the quality of a product is relatively poor, and the active matter content of the product is only 60%. In the late 1970s and early 1980s, Japan's Motoo Koyama invented a method for synthesis of alkanolamide with slightly excess fatty acids and by firstly adding sodium hydroxide, potassium hydroxide, calcium hydroxide, barium hydroxide, sodium methoxide, sodium ethoxide, sodium carbonate, potassium carbonate or an alkali alcoholate of alkanol amine or other alkali catalysts, and an alkanolamide product with an amine value being 50 to 60 mgKOH/g was obtained. Afterwards, on the basis, domestic and foreign operators obtained alkanolamide products with the fatty acid conversion rate up to 98% by optimizing a rate of charge, the type of catalysts, reaction temperatures, nitrogen protection, etc. Since fatty acids and alkanol amine barely have reaction under the temperature lower than 150° C., reaction has to be performed under a higher temperature, and an obtained product has deep color and poor quality. The temperature for synthesizing alkanolamide through reaction of fatty acid low carbon alcohol ester, especially fatty acid methyl ester and alkanol amine is obviously lower than that of the fatty acid method, the reaction is promoted to proceed to the direction of an alkanolamide product by evaporating generated lower alcohols, and therefore the product has relatively light color and relatively high quality. The temperature for synthesizing alkanolamide through reaction of fat and oil, and alkanol amine is lower, and a glycerol by-product generated in the reaction is always an important moisturizing ingredient in a following formula, and thus does not need to be separated.

Compared with the fatty acid method, the alkanolamide surfactant synthesized through the fatty acid low carbon alcohol ester method and the fat and oil method has lighter color and higher quality. Therefore, the fatty acid low carbon alcohol ester method (the fatty acid short chain alcohol ester method) and the fat and oil method are the main methods for synthesizing alkanolamide applied to daily chemicals at present. In recent years, the safety problem of the alkanolamide surfactant causes wide concern, and application is affected mainly because free alkanol amine, especially diethanol amine in the surfactant has the possibility of generating carcinogenic nitrosamine; and residual alkanol amine in the alkanolamide product is generated by, on the one hand, for example, excess alkanol amine adopted in 1:2 or 1:1.5 products to promote reaction to proceed to the direction of the alkanolamide surfactant, and on the other hand, a process where a catalyst is added at a time, in which the activity of the catalyst is lowered in the late reaction period and consequently the conversion rate is lowered. Approaches for reducing residual alkanol amine in the alkanolamide product mainly include eliminating the 1:2 and 1:1.5 alkanolamide products, and improving the activity of catalytic reaction by adding catalysts in a fed-batch mode or intermittently adding the catalysts in batches. As for a 1:1 alkanolamide product, although the process that the catalysts are added in the fed-batch mode or the catalysts are intermittently added in batches can maintain high amidation activity in the late reaction period so as to further greatly reduce the residual quantity of the alkanol amine in the product, the product obtained through the process still has a relatively high residual quantity of the alkanol amine, and new problems of increased process control difficulty and complex process operation are generated. The present disclosure discloses a calcium-based catalyst capable of maintaining good catalytic activity in a whole reaction process, and catalytic synthesis of alkanolamide with low free-amine content through reaction of fat and oil, or fatty acid low carbon alcohol ester and alkanol amine with an approximate stoichiometric ratio.

SUMMARY

The present disclosure discloses a calcium-based catalyst. The catalyst is composed of components in parts by weight: 1 to 20 parts of $Ca(OH)_2$, 20 to 500 parts of KOH and 20 to 500 parts of NaOH.

The present disclosure further discloses a method for preparing the above calcium-based catalyst. The method includes the following steps:

evenly mixing $Ca(OH)_2$, KOH and NaOH according to the above weight parts, and drying to obtain the calcium-based catalyst.

In an embodiment of the present disclosure, the obtained calcium-based catalyst is a granular or spheroidal porous calcium-based catalyst.

In an embodiment of the present disclosure, in the method, CaO or $Ca(OH)_2$ is dispersed in water to be prepared into a 1 wt % to 20 wt % $Ca(OH)_2$ suspension, and then the suspension is used to prepare the calcium-based catalyst in a mixing manner.

In an embodiment of the present disclosure, in the method, solid KOH is dissolved in water or a KOH concentrated solution is diluted so as to be prepared into a 20 to 50 wt % KOH solution, and then the solution is used to prepare the calcium-based catalyst.

In an embodiment of the present disclosure, in the method, solid NaOH is dissolved in water or a NaOH concentrated solution is diluted so as to be prepared into a 20 to 50 wt % NaOH solution, and then the solution is used to prepare the calcium-based catalyst.

In an embodiment of the present disclosure, drying is evaporative drying performed under a temperature of 80° C. to 150° C., or spray drying performed under a temperature of 150° C. to 280° C.

In an embodiment of the present disclosure, the temperature of evaporative drying is preferably 90° C. to 120° C.

In an embodiment of the present disclosure, the temperature of spray drying is preferably 150° C. to 210° C.

The present disclosure further discloses a method for preparing an amide compound. The above calcium-based catalyst is utilized in the method as a catalyst to catalyze amidation of an ester compound and an amine compound.

The present disclosure further discloses a method for preparing an alkanolamide surfactant. The above calcium-based catalyst is utilized in the method as a catalyst to catalyze amidation of an ester compound and alkanol amine, wherein the ester compound includes fat and oil, and/or fatty acid ester.

In an embodiment of the present disclosure, when the ester compound is the fat and oil, a ratio of the amount of substances of the ester compound to the alkanol amine is (1 to 1.05):3.

In an embodiment of the present disclosure, when the ester compound is the fatty acid ester, a ratio of the amount of substances of the ester compound to the alkanol amine is (1 to 1.05):1.

In an embodiment of the present disclosure, an addition amount of the calcium-based catalyst is 0.05 wt % to 2 wt % based on the total mass of the ester compound and the alkanol amine.

In an embodiment of the present disclosure, a reaction temperature of the amidation is 35° C. to 120° C.

In an embodiment of the present disclosure, the fat and oil includes vegetable grease and animal grease. The vegetable grease includes coconut oil, palm kernel oil, palm oil, soybean oil, rapeseed oil, linseed oil and tall oil; and the animal grease includes lard oil, beef tallow, mutton tallow, etc.

In an embodiment of the present disclosure, the fatty acid ester includes methyl caprate, methyl laurate, methyl myristate, methyl palmitate, methyl stearate, methyl 9-hydroxystearate, methyl oleate, methyl linoleate, methyl erucate, ethyl caprate, ethyl laurate, ethyl myristate, ethyl palmitate, ethyl stearate, ethyl 9-hydroxystearate, ethyl oleate, ethyl linoleate, ethyl erucate, or a mixture of the above esters, or mixed fatty acid methyl ester or mixed fatty acid ethyl ester obtained by hydrolytic esterification on natural fat and oil, or mixed fatty acid methyl ester or mixed fatty acid ethyl ester obtained by transesterification on natural fatty acids.

In an embodiment of the present disclosure, the alkanol amine includes diethanol amine, monoethanol amine, methyl monoethanol amine, etc.

In an embodiment of the present disclosure, when the amidation adopts the fat and oil and the alkanol amine as substrates, the method includes: evenly mixing the fat and oil and the alkanol amine according to the ratio of the amount of substances being (1 to 1.05):3, then adding the calcium-based catalyst, and heating a reaction mixture to 35 to 120° C. to react for 4 to 48 h so as to obtain the high-quality alkanolamide surfactant with light color, small smell and low free amine content.

In an embodiment of the present disclosure, when the amidation adopts the fatty acid ester and the alkanol amine as substrates, the method includes: evenly mixing the fatty acid ester and the alkanol amine according to the ratio of the amount of substances being (1 to 1.05):1, then adding the calcium-based catalyst, and reacting for 2 to 12 h at 35 to 120° C. and under the vacuum of −0.01 to −0.1 MPa so as to obtain the high-quality alkanolamide surfactant with light color, small smell and low free amine content.

Beneficial Effects (1) The calcium-based catalyst is adopted in the present disclosure, that is, a compound catalyst containing calcium hydroxide, sodium hydroxide and potassium hydroxide is adopted to catalyze reaction of the fat and oil, or fatty acid short chain alcohol ester and the alkanol amine of a stoichiometric ratio to synthesize the alkanolamide surfactant, and in the reaction process, the slow release feature of the catalyst makes the catalyst still have relatively high catalytic reaction activity in the late reaction period, so that it is guaranteed that the alkanol amine is converted into the alkanolamide surfactant with a high conversion rate.

(2) In the present disclosure, the conversion rate of the alkanol amine is high and is 99% or above, the residual quantity of the alkanol amine in the product is low and is not higher than 1%, and the risk of nitrosamine caused by residual alkanol amine of the product is greatly lowered.

(3) The calcium-based catalyst is adopted in the present disclosure, that is, the compound catalyst containing calcium hydroxide, sodium hydroxide and potassium hydroxide is adopted to catalyze the reaction of the fat and oil, or the fatty acid short chain alcohol ester and the alkanol amine of an approximate stoichiometric ratio to synthesize the alkanolamide surfactant, and in the reaction process, the slow release feature of the catalyst makes the reaction speed in the early reaction period greatly reduced, so that a deepened color of the product caused by poor heat transfer in the synthesis process due to excessively fast reaction in the early period is effectively avoided.

(4) In the present disclosure, the fat and oil, or the fatty acid short chain alcohol ester and the alkanol amine of the approximate stoichiometric ratio react to synthesize the alkanolamide surfactant with a high yield, and the atom utilization rate is high.

BRIEF DESCRIPTION OF FIGURES

The provided FIGURE is a relational graph of a conversion rate of diethanol amine changing with time in Example 11 and Comparative examples 1 to 10.

DETAILED DESCRIPTION

The present disclosure is further illustrated below in conjunction with specific examples, but the present disclosure is not limited in any way, and any change or replacement made based on teachings of the present disclosure belongs to the scope of protection of the present disclosure.

Example 1

100 g of an 8 wt % $Ca(OH)_2$ suspension, 600 g of a 40 wt % KOH solution and 200 g of a 20 wt % NaOH solution were quickly added into a 2 L reaction kettle with an intense mixing device at the same time and were intensely mixed for 30 minutes, then moisture was evaporated under 130° C. to obtain 290 g of a blocky white solid, and the blocky solid was smashed and used to catalytically synthesize an alkanolamide surfactant.

Example 2

100 g of an 1 wt % $Ca(OH)_2$ suspension, 900 g of a 40 wt % KOH solution and 200 g of a 20 wt % NaOH solution were quickly added into a 2 L reaction kettle with an intense mixing device at the same time and were intensely mixed for 30 minutes, then moisture was evaporated under 140° C. to obtain 410 g of a blocky white solid, and the blocky solid was smashed and used to catalytically synthesize an alkanolamide surfactant.

Example 3

100 g of an 1 wt % Ca(OH)$_2$ suspension, 1000 g of a 20 wt % KOH solution and 200 g of a 30 wt % NaOH solution were quickly added into a 2 L reaction kettle with an intense mixing device at the same time and were intensely mixed for 30 minutes, then moisture was evaporated under 140° C. to obtain 275 g of a blocky white solid, and the blocky solid was smashed and used to catalytically synthesize an alkanolamide surfactant.

Example 4

100 g of an 1 wt % Ca(OH)$_2$ suspension, 1000 g of a 50 wt % KOH solution and 200 g of a 30 wt % NaOH solution were quickly added into a 2 L reaction kettle with an intense mixing device at the same time and were intensely mixed for 30 minutes, then moisture was evaporated under 90° C. to obtain 580 g of a blocky white solid, and the blocky solid was smashed and used to catalytically synthesize an alkanolamide surfactant.

Example 5

100 g of an 4 wt % Ca(OH)$_2$ suspension, 500 g of a 30 wt % KOH solution and 600 g of a 50 wt % NaOH solution were quickly added into a 2 L reaction kettle with an intense mixing device at the same time and were intensely mixed for 30 minutes, then moisture was evaporated under 90° C. to obtain 454 g of a blocky white solid, and the blocky solid was smashed and used to catalytically synthesize an alkanolamide surfactant.

Example 6

1,000 g of a 7 wt % Ca(OH)$_2$ suspension, 5,000 g of a 50 wt % KOH solution and 6,000 g of a 50 wt % NaOH solution were pumped in proportion into a static mixer with the diameter of 2 cm and the length of 60 cm through a metering pump within 30 min and were evenly mixed, a mixed suspension was dried in a small spray drier with a hot air temperature of 200° C. to obtain 5.5 kg of a fluffy catalyst, and the catalyst could be directly used to catalytically synthesize an alkanolamide surfactant.

Example 7

1,000 g of a 3 wt % Ca(OH)$_2$ suspension, 8,000 g of a 40 wt % KOH solution and 4,000 g of a 30 wt % NaOH solution were pumped in proportion into a static mixer with the diameter of 2 cm and the length of 60 cm through a metering pump within 30 min and were evenly mixed, a mixed suspension was dried in a small spray drier with a hot air temperature of 210° C. to obtain 4.5 kg of a fluffy catalyst, and the catalyst could be directly used to catalytically synthesize an alkanolamide surfactant.

Example 8

100 g of a 2 wt % Ca(OH)$_2$ suspension, 900 g of a 30 wt % KOH solution and 300 g of a 30 wt % NaOH solution were pumped in proportion into a static mixer with the diameter of 2 cm and the length of 60 cm through a metering pump within 10 min and were evenly mixed, moisture in a mixed suspension was evaporated under 140° C. and dried to obtain 370 g of a blocky white solid, and the blocky solid was smashed and used to catalytically synthesize an alkanolamide surfactant.

Example 9

100 g of a 9 wt % Ca(OH)$_2$ suspension, 200 g of a 20 wt % KOH solution and 300 g of a 30 wt % NaOH solution were pumped in proportion into a static mixer with the diameter of 2 cm and the length of 60 cm through a metering pump within 10 min and were evenly mixed, moisture in a mixed suspension was evaporated under 140° C. and dried to obtain 195 g of a blocky white solid, and the blocky solid was smashed and used to catalytically synthesize an alkanolamide surfactant.

Example 10

100 g of a 6 wt % Ca(OH)$_2$ suspension, 100 g of a 50 wt % KOH solution and 500 g of a 35 wt % NaOH solution were pumped in proportion into a static mixer with the diameter of 2 cm and the length of 60 cm through a metering pump within 10 min and were evenly mixed, moisture in a mixed suspension was evaporated under 120° C. and dried to obtain 242 g of a blocky white solid, and the blocky solid was smashed and used to catalytically synthesize an alkanolamide surfactant.

Example 11

2.67 kg of refined coconut oil with a saponification value of 251.6 mgKOH/g and 1.24 kg of diethanol amine were added into a reactor with heating, condensing, reflux, temperature control and mixing functions and were evenly mixed, and then 19.7 g of the catalyst in Example 3 was added to react for 4 h under 80° C. to obtain faint-yellow transparent liquid with a color lighter than that of the raw material refined coconut oil. The catalyst maintained good reaction activity in a whole reaction process, no rapid and intense reaction occurred in the early reaction period, so the color of the product was light; and the catalyst maintained good reaction activity in the whole reaction process, so the conversion rate of the diethanol amine after reaction was up to 99.8%, and the residual quantity of the diethanol amine in the product was less than 0.016 wt %.

Example 12

1.34 kg of refined coconut oil with a saponification value of 251.6 mgKOH/g and 1.34 kg of methyl monoethanol amine were added into a reactor with heating, condensing, reflux, temperature control and mixing functions and were evenly mixed, and then 8.92 g of the catalyst in Example 4 was added to react for 8 h under 35° C. to obtain faint-yellow transparent liquid with a color lighter than that of the raw material refined coconut oil. The catalyst maintained good reaction activity in a whole reaction process, no rapid and intense reaction occurred in the early reaction period, so the color of the product was light; and the catalyst maintained good reaction activity in the whole reaction process, so the conversion rate of the methyl monoethanol amine after reaction was up to 99.5%, and the residual quantity of the methyl monoethanol amine in the product was less than 0.1 wt %.

Example 13

2.12 kg of palm kernel oil with a saponification value of 238.8 mgKOH/g and 0.65 kg of methyl monoethanol amine were added into a reactor with heating, condensing, reflux, temperature control and mixing functions and were evenly mixed, and then 13.85 g of the catalyst in Example 6 was added to react for 7 h under 55° C. to obtain faint-yellow transparent liquid with a color lighter than that of the raw material palm kernel oil. The catalyst maintained good reaction activity in a whole reaction process, no rapid and intense reaction occurred in the early reaction period, so the color of the product was light; and the catalyst maintained good reaction activity in the whole reaction process, so the conversion rate of the methyl monoethanol amine after reaction was up to 99.8%, and the residual quantity of the methyl monoethanol amine in the product was less than 0.05 wt %.

Example 14

0.86 kg of cottonseed oil with a saponification value of 195.7 mgKOH/g and 0.18 kg of monoethanol amine were added into a reactor with heating, condensing, reflux, temperature control and mixing functions and were evenly mixed, and then 5.20 g of the catalyst in Example 1 was added to react for 9 h under 120° C. to obtain faint-yellow transparent liquid with a color lighter than that of the raw material cottonseed oil, and a milky white solid was obtained after cooling. The catalyst maintained good reaction activity in a whole reaction process, no rapid and intense reaction occurred in the early reaction period, so the color of the product was light; and the catalyst maintained good reaction activity in the whole reaction process, so the conversion rate of the monoethanol amine after reaction was up to 99.6%, and the residual quantity of the monoethanol amine in the product was less than 0.07 wt %.

Example 15

1.85 kg of peanut oil with a saponification value of 181.8 mgKOH/g and 0.35 kg of monoethanol amine were added into a reactor with heating, condensing, reflux, temperature control and mixing functions and were evenly mixed, and then 11.02 g of the catalyst in Example 2 was added to react for 5 h under nitrogen atmosphere at 100° C. to obtain faint-yellow transparent liquid with a color lighter than that of the raw material c peanut oil, and a milky yellow solid was obtained after cooling. The catalyst maintained good reaction activity in a whole reaction process, no rapid and intense reaction occurred in the early reaction period, so the color of the product was light; and the catalyst maintained good reaction activity in the whole reaction process, so the conversion rate of the monoethanol amine after reaction was up to 99.55%, and the residual quantity of the monoethanol amine in the product was less than 0.07 wt %.

Example 16

0.84 kg of palm oil with a saponification value of 201.4 mgKOH/g and 0.31 kg of diethanol amine were added into a reactor with heating, condensing, reflux, temperature control and mixing functions and were evenly mixed, and then 5.20 g of the catalyst in Example 1 was added to react for 8 h under 120° C. to obtain faint-yellow transparent liquid with a color lighter than that of the raw material palm oil. The catalyst maintained good reaction activity in a whole reaction process, no rapid and intense reaction occurred in the early reaction period, so the color of the product was light; and the catalyst maintained good reaction activity in the whole reaction process, so the conversion rate of the diethanol amine after reaction was up to 99.6%, and the residual quantity of the diethanol amine in the product was less than 0.05 wt %.

Example 17

0.87 kg of safflower oil with a saponification value of 193.1 mg KOH/g and 0.22 kg of methyl monoethanol amine were added into a reactor with heating, condensing, reflux, temperature control and mixing functions and were evenly mixed, and then 1.96 g of the catalyst in Example 10 was added to react for 16 h under nitrogen atmosphere at 70° C. to obtain faint-yellow transparent liquid with a color lighter than that of the raw material safflower oil. The catalyst maintained good reaction activity in a whole reaction process, no rapid and intense reaction occurred in the early reaction period, so the color of the product was light; and the catalyst maintained good reaction activity in the whole reaction process, so the conversion rate of the methyl monoethanol amine after reaction was up to 99.7%, and the residual quantity of the methyl monoethanol amine in the product was less than 0.06 wt %.

Example 18

0.86 kg of corn oil with a saponification value of 196.5 mg KOH/g and 0.17 kg of monoethanol amine were added into a reactor with heating, condensing, reflux, temperature control and mixing functions and were evenly mixed, and then 10.43 g of the catalyst in Example 6 was added to react for 8 h under 90° C. to obtain faint-yellow transparent liquid with a color lighter than that of the raw material corn oil, and a milky white solid was obtained after cooling. The catalyst maintained good reaction activity in a whole reaction process, no rapid and intense reaction occurred in the early reaction period, so the color of the product was light; and the catalyst maintained good reaction activity in the whole reaction process, so the conversion rate of the monoethanol amine after reaction was up to 99.8%, and the residual quantity of the monoethanol amine in the product was less than 0.04 wt %.

Example 19

0.89 kg of rapeseed oil with a saponification value of 175.4 mg KOH/g and 0.18 kg of monoethanol amine were added into a reactor with heating, condensing, reflux, temperature control and mixing functions and were evenly mixed, and then 10.52 g of the catalyst in Example 7 was added to react for 4 h under 100° C. to obtain faint-yellow transparent liquid with a color lighter than that of the raw material rapeseed oil, and a yellowish solid was obtained after cooling. The catalyst maintained good reaction activity in a whole reaction process, no rapid and intense reaction occurred in the early reaction period, so the color of the product was light; and the catalyst maintained good reaction activity in the whole reaction process, so the conversion rate of the monoethanol amine after reaction was up to 99.6%, and the residual quantity of the monoethanol amine in the product was less than 0.07 wt %.

Example 20

2.63 kg of sunflower seed oil with a saponification value of 191.7 mg KOH/g and 0.94 kg of diethanol amine were added into a reactor with heating, condensing, reflux, temperature control and mixing functions and were evenly mixed, and then 15.09 g of the catalyst in Example 9 was added to react for 6 h under 35° C. to obtain faint-yellow transparent liquid with a color lighter than that of the raw material sunflower seed oil. The catalyst maintained good reaction activity in a whole reaction process, no rapid and intense reaction occurred in the early reaction period, so the color of the product was light; and the catalyst maintained good reaction activity in the whole reaction process, so the conversion rate of the diethanol amine after reaction was up to 99.8%, and the residual quantity of the diethanol amine in the product was less than 0.05 wt %.

Example 21

2.68 kg of coconut oil with a saponification value of 252.0 mg KOH/g and 0.72 kg of monoethanol amine were added into a reactor with heating, condensing, reflux, temperature control and mixing functions and were evenly mixed, and then 16.90 g of the catalyst in Example 8 was added to react for 6 h under 90° C. to obtain faint-yellow transparent liquid with a color lighter than that of the raw material coconut oil, and a milky white solid was obtained after cooling. The catalyst maintained good reaction activity in a whole reaction process, no rapid and intense reaction occurred in the early reaction period, so the color of the product was light; and the catalyst maintained good reaction activity in the whole reaction process, so the conversion rate of the monoethanol amine after reaction was up to 99.7%, and the residual quantity of the monoethanol amine in the product was less than 0.05 wt %.

Example 22

2.68 kg of coconut oil with a saponification value of 252.0 mg KOH/g and 1.20 kg of diethanol amine were added into a reactor with heating, condensing, reflux, temperature control and mixing functions and were evenly mixed, and then 19.93 g of the catalyst in Example 5 was added to react for 8 h under 60° C. to obtain faint-yellow transparent liquid with a color lighter than that of the raw material coconut oil. The catalyst maintained good reaction activity in a whole reaction process, no rapid and intense reaction occurred in the early reaction period, so the color of the product was light; and the catalyst maintained good reaction activity in the whole reaction process, so the conversion rate of the diethanol amine after reaction was up to 99.9%, and the residual quantity of the diethanol amine in the product was less than 0.02 wt %.

Example 23

2.68 kg of coconut oil with a saponification value of 252.0 mg KOH/g and 0.89 kg of methyl monoethanol amine were added into a reactor with heating, condensing, reflux, temperature control and mixing functions and were evenly mixed, and then 17.84 g of the catalyst in Example 10 was added to react for 3 h under 120° C. to obtain faint-yellow transparent liquid with a color lighter than that of the raw material coconut oil. The catalyst maintained good reaction activity in a whole reaction process, no rapid and intense reaction occurred in the early reaction period, so the color of the product was light; and the catalyst maintained good reaction activity in the whole reaction process, so the conversion rate of the methyl monoethanol amine after reaction was up to 99.9%, and the residual quantity of the methyl monoethanol amine in the product was less than 0.03 wt %.

Example 24

4.3 kg of soybean oil with a saponification value of 195.7 mg KOH/g and 1.50 kg of diethanol amine were added into a reactor with heating, condensing, reflux, temperature control and mixing functions and were evenly mixed, and then 9.63 g of the catalyst in Example 5 was added to react for 9 h under 60° C. to obtain faint-yellow transparent liquid with a color lighter than that of the raw material soybean oil. The catalyst maintained good reaction activity in a whole reaction process, no rapid and intense reaction occurred in the early reaction period, so the color of the product was light; and the catalyst maintained good reaction activity in the whole reaction process, so the conversion rate of the diethanol amine after reaction was up to 99.7%, and the residual quantity of the diethanol amine in the product was less than 0.06 wt %.

Example 25

0.70 kg of palm kernel oil with a saponification value of 238.7 mg KOH/g and 0.22 kg of methyl monoethanol amine were added into a reactor with heating, condensing, reflux, temperature control and mixing functions and were evenly mixed, and then 4.66 g of the catalyst in Example 4 was added to react for 12 h under 30° C. to obtain faint-yellow transparent liquid with a color lighter than that of the raw material palm kernel oil. The catalyst maintained good reaction activity in a whole reaction process, no rapid and intense reaction occurred in the early reaction period, so the color of the product was light; and the catalyst maintained good reaction activity in the whole reaction process, so the conversion rate of the methyl monoethanol amine after reaction was up to 99.6%, and the residual quantity of the methyl monoethanol amine in the product was less than 0.1 wt %.

Example 26

1.41 kg of palm kernel oil with a saponification value of 238.7 mg KOH/g and 0.37 kg of monoethanol amine were added into a reactor with heating, condensing, reflux, temperature control and mixing functions and were evenly mixed, and then 8.95 g of the catalyst in Example 6 was added to react for 3 h under 100° C. to obtain faint-yellow transparent liquid with a color lighter than that of the raw material palm kernel oil, and a white solid was obtained after cooling. The catalyst maintained good reaction activity in a whole reaction process, no rapid and intense reaction occurred in the early reaction period, so the color of the product was light; and the catalyst maintained good reaction activity in the whole reaction process, so the conversion rate of the monoethanol amine after reaction was up to 99.8%, and the residual quantity of the monoethanol amine in the product was less than 0.05 wt %.

Example 27

2.82 kg of palm kernel oil with a saponification value of 238.7 mg KOH/g and 0.69 kg of monoethanol amine were added into a reactor with heating, condensing, reflux, temperature control and mixing functions and were evenly mixed, and then 17.65 g of the catalyst in Example 6 was added to react for 7 h under 90° C. to obtain faint-yellow transparent liquid with a color lighter than that of the raw material palm kernel oil, and a white solid was obtained after cooling. The catalyst maintained good reaction activity in a whole reaction process, no rapid and intense reaction occurred in the early reaction period, so the color of the product was light; and the catalyst maintained good reaction activity in the whole reaction process, so the conversion rate of the monoethanol amine after reaction was up to 99.7%, and the residual quantity of the monoethanol amine in the product was less than 0.06 wt %.

Example 28

0.93 kg of methyl caprate and 0.36 kg of methyl monoethanol amine were added into a reactor with heating, condensing, reflux, temperature control, mixing and vacuum devices and were evenly mixed, then 10.33 g of the catalyst in Example 6 was added to react for 4 h under 40° C. and a vacuum degree with gauge pressure of −0.07 MPa to obtain colorless transparent liquid, and a white solid was obtained after cooling. No rapid and intense reaction occurred in the early reaction period, so the color of the product was light; and the catalyst maintained good reaction activity in a whole reaction process, so the conversion rate of the methyl monoethanol amine in reaction was up to 99.7%, and the residual quantity of the methyl monoethanol amine in the product was less than 0.05 wt %.

Example 29

0.428 kg of methyl laurate and 0.148 kg of methyl monoethanol amine were added into a reactor with heating, condensing, reflux, temperature control, mixing and vacuum devices and were evenly mixed, then 4.41 g of the catalyst in Example 3 was added to react for 3 h under 50° C. and a vacuum degree with gauge pressure of −0.05 MPa to obtain colorless transparent liquid. No rapid and intense reaction occurred in the early reaction period, so the color of the product was light; and the catalyst maintained good reaction activity in a whole reaction process, so the conversion rate of the methyl monoethanol amine in reaction was up to 99.8%, and the residual quantity of the methyl monoethanol amine in the product was less than 0.06 wt %.

Example 30

0.242 kg of methyl myristate and 0.058 kg of monoethanol amine were added into a reactor with heating, condensing, reflux, temperature control, mixing and vacuum devices and were evenly mixed, then 2.13 g of the catalyst in Example 5 was added to react for 3 h under 80° C. and a vacuum degree with gauge pressure of −0.07 MPa to obtain colorless transparent liquid, and a white solid was obtained after cooling. No rapid and intense reaction occurred in the early reaction period, so the color of the product was light; and the catalyst maintained good reaction activity in a whole reaction process, so the conversion rate of the monoethanol amine in reaction was up to 99.8%, and the residual quantity of the monoethanol amine in the product was less than 0.03 wt %.

Example 31

0.540 kg of methyl palmitate and 0.119 kg of monoethanol amine were added into a reactor with heating, condensing, reflux, temperature control, mixing and vacuum devices and were evenly mixed, then 4.55 g of the catalyst in Example 2 was added to react for 3 h under 80° C. and a vacuum degree with gauge pressure of −0.06 MPa to obtain colorless transparent liquid, and a white solid was obtained after cooling. No rapid and intense reaction occurred in the early reaction period, so the color of the product was light; and the catalyst maintained good reaction activity in a whole reaction process, so the conversion rate of the monoethanol amine in reaction was up to 99.5%, and the residual quantity of the monoethanol amine in the product was less than 0.1 wt %.

Example 32

0.298 kg of methyl stearate and 0.059 kg of monoethanol amine were added into a reactor with heating, condensing, reflux, temperature control, mixing and vacuum devices and were evenly mixed, then 2.42 g of the catalyst in Example 7 was added to react for 4 h under 75° C. and a vacuum degree with gauge pressure of −0.05 MPa to obtain colorless transparent liquid, and a white solid was obtained after cooling. No rapid and intense reaction occurred in the early reaction period, so the color of the product was light; and the catalyst maintained good reaction activity in a whole reaction process, so the conversion rate of the monoethanol amine in reaction was up to 99.5%, and the residual quantity of the monoethanol amine in the product was less than 0.09 wt %.

Example 33

1.18 kg of methyl oleate and 0.411 kg of diethanol amine were added into a reactor with heating, condensing, reflux, temperature control, mixing and vacuum devices and were evenly mixed, then 12.22 g of the catalyst in Example 3 was added to react for 6 h under 70° C. and a vacuum degree with gauge pressure of −0.05 MPa to obtain colorless transparent liquid. No rapid and intense reaction occurred in the early reaction period, so the color of the product was light; and the catalyst maintained good reaction activity in a whole reaction process, so the conversion rate of the diethanol amine in reaction was up to 99.9%, and the residual quantity of the diethanol amine in the product was less than 0.03 wt %.

Example 34

0.588 kg of methyl linoleate and 0.148 kg of methyl monoethanol amine were added into a reactor with heating, condensing, reflux, temperature control, mixing and vacuum devices and were evenly mixed, then 5.24 g of the catalyst in Example 8 was added to react for 7 h under 105° C. and a vacuum degree with gauge pressure of −0.05 MPa to obtain colorless transparent liquid. No rapid and intense reaction occurred in the early reaction period, so the color of the product was light; and the catalyst maintained good reaction activity in a whole reaction process, so the conversion rate of the methyl monoethanol amine in reaction was up to 99.8%, and the residual quantity of the methyl monoethanol amine in the product was less than 0.04 wt %.

Example 35

1.76 kg of methyl erucate and 0.36 kg of methyl monoethanol amine were added into a reactor with heating, condensing, reflux, temperature control, mixing and vacuum devices and were evenly mixed, then 10.68 g of the catalyst in Example 2 was added to react for 6 h under 60° C. and a vacuum degree with gauge pressure of −0.06 MPa to obtain colorless transparent liquid. No rapid and intense reaction occurred in the early reaction period, so the color of the product was light; and the catalyst maintained good reaction activity in a whole reaction process, so the conversion rate of the methyl monoethanol amine in reaction was up to 99.9%, and the residual quantity of the methyl monoethanol amine in the product was less than 0.03 wt %.

Example 36

0.80 kg of ethyl caprate and 0.24 kg of monoethanol amine were added into a reactor with heating, condensing, reflux, temperature control, mixing and vacuum devices and were evenly mixed, then 5.23 g of the catalyst in Example 9 was added to react for 8 h under 80° C. and a vacuum degree with gauge pressure of −0.04 MPa to obtain colorless transparent liquid, and a milky white solid was obtained after cooling. No rapid and intense reaction occurred in the early reaction period, so the color of the product was light; and the catalyst maintained good reaction activity in a whole reaction process, so the conversion rate of the monoethanol amine in reaction was up to 99.9%, and the residual quantity of the monoethanol amine in the product was less than 0.02 wt %.

Example 37

0.684 kg of ethyl laurate and 0.183 kg of monoethanol amine were added into a reactor with heating, condensing, reflux, temperature control, mixing and vacuum devices and were evenly mixed, then 11.56 g of the catalyst in Example 3 was added to react for 5 h under 90° C. and a vacuum degree with gauge pressure of −0.05 MPa to obtain colorless transparent liquid, and a milky white solid was obtained after cooling. No rapid and intense reaction occurred in the early reaction period, so the color of the product was light; and the catalyst maintained good reaction activity in a whole reaction process, so the conversion rate of the monoethanol amine in reaction was up to 99.8%, and the residual quantity of the monoethanol amine in the product was less than 0.02 wt %.

Example 38

0.768 kg of ethyl myristate and 0.299 kg of diethanol amine were added into a reactor with heating, condensing, reflux, temperature control, mixing and vacuum devices and were evenly mixed, then 20.75 g of the catalyst in Example 2 was added to react for 7 h under 40° C. and a vacuum degree with gauge pressure of −0.05 MPa to obtain colorless transparent liquid. No rapid and intense reaction occurred in the early reaction period, so the color of the product was light; and the catalyst maintained good reaction activity in a whole reaction process, so the conversion rate of the diethanol amine in reaction was up to 99.6%, and the residual quantity of the diethanol amine in the product was less than 0.02 wt %.

Example 39

0.852 kg of ethyl palmitate and 0.311 kg of diethanol amine were added into a reactor with heating, condensing, reflux, temperature control, mixing and vacuum devices and were evenly mixed, then 9.00 g of the catalyst in Example 10 was added to react for 6 h under 50° C. and a vacuum degree with gauge pressure of −0.08 MPa to obtain colorless transparent liquid. No rapid and intense reaction occurred in the early reaction period, so the color of the product was light; and the catalyst maintained good reaction activity in a whole reaction process, so the conversion rate of the diethanol amine in reaction was up to 99.6%, and the residual quantity of the diethanol amine in the product was less than 0.1 wt %.

Example 40

0.312 kg of ethyl stearate and 0.075 kg of methyl monoethanol amine were added into a reactor with heating, condensing, reflux, temperature control, mixing and vacuum devices and were evenly mixed, then 7.55 g of the catalyst in Example 4 was added to react for 8 h under 70° C. and a vacuum degree with gauge pressure of −0.05 MPa to obtain colorless transparent liquid. No rapid and intense reaction occurred in the early reaction period, so the color of the product was light; and the catalyst maintained good reaction activity in a whole reaction process, so the conversion rate of the methyl monoethanol amine in reaction was up to 99.8%, and the residual quantity of the methyl monoethanol amine in the product was less than 0.06 wt %.

Example 41

0.62 kg of ethyl stearate and 0.15 kg of methyl monoethanol amine were added into a reactor with heating, condensing, reflux, temperature control, mixing and vacuum devices and were evenly mixed, then 4.49 g of the catalyst in Example 7 was added to react for 4 h under 60° C. and a vacuum degree with gauge pressure of −0.05 MPa to obtain colorless transparent liquid. No rapid and intense reaction occurred in the early reaction period, so the color of the product was light; and the catalyst maintained good reaction activity in a whole reaction process, so the conversion rate of the methyl monoethanol amine in reaction was up to 99.7%, and the residual quantity of the methyl monoethanol amine in the product was less than 0.05 wt %.

Example 42

1.23 kg of ethyl linoleate and 0.23 kg of monoethanol amine were added into a reactor with heating, condensing, reflux, temperature control, mixing and vacuum devices and were evenly mixed, then 7.38 g of the catalyst in Example 3 was added to react for 6 h under 100° C. and a vacuum degree with gauge pressure of −0.05 MPa to obtain colorless transparent liquid, and a white solid was obtained after cooling. No rapid and intense reaction occurred in the early reaction period, so the color of the product was light; and the catalyst maintained good reaction activity in a whole reaction process, so the conversion rate of the monoethanol amine in reaction was up to 99.9%, and the residual quantity of the monoethanol amine in the product was less than 0.02 wt %.

Example 43

1.05 kg of ethyl erucate and 0.17 kg of monoethanol amine were added into a reactor with heating, condensing, reflux, temperature control, mixing and vacuum devices and were evenly mixed, then 6.18 g of the catalyst in Example 10 was added to react for 6 h under 120° C. and a vacuum degree with gauge pressure of −0.03 MPa to obtain colorless transparent liquid, and a white solid was obtained after cooling. No rapid and intense reaction occurred in the early reaction period, so the color of the product was light; and the catalyst maintained good reaction activity in a whole reaction process, so the conversion rate of the monoethanol amine in reaction was up to 99.8%, and the residual quantity of the monoethanol amine in the product was less than 0.03 wt %.

Example 44

0.21 kg of methyl laurate, 0.24 kg of methyl myristate and 0.12 kg of monoethanol amine were added into a reactor with heating, condensing, reflux, temperature control, mixing and vacuum devices and were evenly mixed, then 2.90 g of the catalyst in Example 5 was added to react for 6 h under 100° C. and a vacuum degree with gauge pressure of −0.04 MPa to obtain colorless transparent liquid, and a white solid was obtained after cooling. No rapid and intense reaction occurred in the early reaction period, so the color of the product was light; and the catalyst maintained good reaction activity in a whole reaction process, so the conversion rate of the monoethanol amine in reaction was up to 99.9%, and the residual quantity of the monoethanol amine in the product was less than 0.02 wt %.

Example 45

0.675 kg of methyl palmitate, 0.78 kg of methyl stearate and 0.51 kg of diethanol amine were added into a reactor with heating, condensing, reflux, temperature control, mixing and vacuum devices and were evenly mixed, then 9.7 g of the catalyst in Example 10 was added to react for 4 h under 56° C. and a vacuum degree with gauge pressure of −0.06 MPa to obtain colorless transparent liquid. No rapid and intense reaction occurred in the early reaction period, so the color of the product was light; and the catalyst maintained good reaction activity in a whole reaction process, so the conversion rate of the diethanol amine in reaction was up to 99.6%, and the residual quantity of the diethanol amine in the product was less than 0.1 wt %.

Example 46

0.448 kg of methyl cocoate and 0.145 kg of methyl monoethanol amine were added into a reactor with heating, condensing, reflux, temperature control, mixing and vacuum devices and were evenly mixed, then 3.0 g of the catalyst in Example 6 was added to react for 8 h under 80° C. and a vacuum degree with gauge pressure of −0.06 MPa to obtain colorless transparent liquid. No rapid and intense reaction occurred in the early reaction period, so the color of the product was light; and the catalyst maintained good reaction activity in a whole reaction process, so the conversion rate of the methyl monoethanol amine in reaction was up to 99.7%, and the residual quantity of the methyl monoethanol amine in the product was less than 0.07 wt %.

Example 47

0.472 kg of methyl palm kernelate and 0.15 kg of methyl monoethanol amine were added into a reactor with heating, condensing, reflux, temperature control, mixing and vacuum devices and were evenly mixed, then 3.11 g of the catalyst in Example 5 was added to react for 10 h under 64° C. and a vacuum degree with gauge pressure of −0.05 MPa to obtain colorless transparent liquid. No rapid and intense reaction occurred in the early reaction period, so the color of the product was light; and the catalyst maintained good reaction activity in a whole reaction process, so the conversion rate of the methyl monoethanol amine in reaction was up to 99.9%, and the residual quantity of the methyl monoethanol amine in the product was less than 0.02 wt %.

Example 48

0.867 kg of methyl soyate and 0.308 kg of diethanol amine were added into a reactor with heating, condensing, reflux, temperature control, mixing and vacuum devices and were evenly mixed, then 5.93 g of the catalyst in Example 10 was added to react for 2 h under 70° C. and a vacuum degree with gauge pressure of −0.05 MPa to obtain colorless transparent liquid. No rapid and intense reaction occurred in the early reaction period, so the color of the product was light; and the catalyst maintained good reaction activity in a whole reaction process, so the conversion rate of the diethanol amine in reaction was up to 99.6%, and the residual quantity of the diethanol amine in the product was less than 0.09 wt %.

Example 49

0.952 kg of ethyl cocoate and 0.234 kg of methyl monoethanol amine were added into a reactor with heating, condensing, reflux, temperature control, mixing and vacuum devices and were evenly mixed, then 6.00 g of the catalyst in Example 8 was added to react for 8 h under 75° C. and a vacuum degree with gauge pressure of −0.05 MPa to obtain colorless transparent liquid. No rapid and intense reaction occurred in the early reaction period, so the color of the product was light; and the catalyst maintained good reaction activity in a whole reaction process, so the conversion rate of the methyl monoethanol amine in reaction was up to 99.7%, and the residual quantity of the methyl monoethanol amine in the product was less than 0.1 wt %.

Example 50

0.223 kg of coconut oil, 0.446 kg of palm kernel oil and 0.668 kg of methyl monoethanol amine were added into a reactor with heating, condensing, reflux, temperature control, mixing and vacuum devices and were evenly mixed, then 12.8 g of the catalyst in Example 3 was added to react for 12 h under 40° C. to obtain colorless transparent liquid. No rapid and intense reaction occurred in the early reaction period, so the color of the product was light; and the catalyst maintained good reaction activity in a whole reaction process, so the conversion rate of the methyl monoethanol amine in reaction was up to 99.6%, and the residual quantity of the methyl monoethanol amine in the product was less than 0.08 wt %.

Comparative Example 1

2.67 kg of refined coconut oil with a saponification value of 251.6 mg KOH/g and 1.24 kg of diethanol amine were added into a reactor with heating, condensing, reflux, temperature control and mixing functions and were evenly mixed, and then 20.0 g of sodium methoxide was added to react for 4 h under 80° C. to obtain deep-yellow transparent liquid, wherein the conversion rate of the diethanol amine was 94.6%; and the residual quantity of the diethanol amine in the product was greater than 1%.

Comparative Example 2

267 g of refined coconut oil with a saponification value of 251.6 mg KOH/g and 124 g of diethanol amine were added into a reactor with heating, condensing, reflux, temperature control and mixing functions and were evenly mixed, and then 2.0 g of sodium methoxide was added to react for 4 h under 80° C. to obtain deep-yellow transparent liquid, wherein the conversion rate of the diethanol amine was 92.8%; and the residual quantity of the diethanol amine in the product was greater than 1%.

Comparative Example 3

267 g of refined coconut oil with a saponification value of 251.6 mg KOH/g and 124 g of diethanol amine were added into a reactor with heating, condensing, reflux, temperature control and mixing functions and were evenly mixed, and then 2.0 g of KOH was added to react for 4 h under 80° C. to obtain deep-yellow transparent liquid, wherein the conversion rate of the diethanol amine was 89.8%; and the residual quantity of the diethanol amine in the product was greater than 1%.

Comparative Example 4

267 g of refined coconut oil with a saponification value of 251.6 mg KOH/g and 124 g of diethanol amine were added into a reactor with heating, condensing, reflux, temperature control and mixing functions and were evenly mixed, and then 2.0 g of NaOH was added to react for 4 h under 80° C. to obtain deep-yellow transparent liquid, wherein the conversion rate of the diethanol amine was 84.4%; and the residual quantity of the diethanol amine in the product was greater than 1%.

Comparative Example 5

267 g of refined coconut oil with a saponification value of 251.6 mg KOH/g and 124 g of diethanol amine were added into a reactor with heating, condensing, reflux, temperature control and mixing functions and were evenly mixed, and then 2.0 g of $Ca(OH)_2$ was added to react for 4 h under 80° C. to obtain deep-yellow transparent liquid, wherein the conversion rate of the diethanol amine was 1.8%.

Comparative Example 6

267 g of refined coconut oil with a saponification value of 251.6 mg KOH/g and 124 g of diethanol amine were added into a reactor with heating, condensing, reflux, temperature control and mixing functions and were evenly mixed, and then 2.0 g of CaO was added to react for 4 h under 80° C. to obtain deep-yellow transparent liquid, wherein the conversion rate of the diethanol amine was 3.7%.

Comparative Example 7

100 g of an 8 wt % $Ca(OH)_2$ suspension and 200 g of a 20 wt % NaOH solution were quickly added into a 2 L reaction kettle with an intense mixing device at the same time and were intensely mixed for 30 minutes, then moisture was evaporated under 130° C. to obtain a blocky white solid, and the blocky solid was smashed and used to catalytically synthesize an alkanolamide surfactant.

267 g of refined coconut oil with a saponification value of 251.6 mg KOH/g and 124 g of diethanol amine were added into a reactor with heating, condensing, reflux, temperature control and mixing functions and were evenly mixed, then 2.0 g of the $Ca(OH)_2$ and NaOH compound catalyst was added to react for 4 h under 80° C. to obtain faint-yellow transparent liquid, and the liquid was layered after being cooled to a room temperature, wherein the conversion rate of the diethanol amine was 37.66%.

Comparative Example 8

100 g of an 8 wt % $Ca(OH)_2$ suspension and 600 g of a 40 wt % KOH solution were quickly added into a 2 L reaction kettle with an intense mixing device at the same time and were intensely mixed for 30 minutes, then moisture was evaporated under 130° C. to obtain a blocky white solid, and the blocky solid was smashed and used to catalytically synthesize an alkanolamide surfactant.

267 g of refined coconut oil with a saponification value of 251.6 mg KOH/g and 124 g of diethanol amine were added into a reactor with heating, condensing, reflux, temperature control and mixing functions and were evenly mixed, then 2.0 g of the $Ca(OH)_2$ and KOH compound catalyst was added to react for 4 h under 80° C. to obtain faint-yellow transparent liquid, and the liquid was layered after being cooled to a room temperature, wherein the conversion rate of the diethanol amine was 77.52%.

Comparative Example 9

600 g of a 40 wt % KOH solution and 200 g of a 20 wt % NaOH solution were quickly added into a 2 L reaction kettle with an intense mixing device at the same time and were intensely mixed for 30 minutes, then moisture was evaporated under 130° C. to obtain a blocky white solid, and the blocky solid was smashed and used to catalytically synthesize an alkanolamide surfactant.

267 g of refined coconut oil with a saponification value of 251.6 mg KOH/g and 124 g of diethanol amine were added into a reactor with heating, condensing, reflux, temperature control and mixing functions and were evenly mixed, then 2.0 g of the NaOH and KOH compound catalyst was added to react for 4 h under 80° C. to obtain faint-yellow transparent liquid, and the liquid was layered after being cooled to a room temperature, wherein the conversion rate of the diethanol amine was 88.12%.

Comparative Example 10

240 g of KOH and 40 g of NaOH were ground and mixed evenly, then moisture in a ground KOH and NaOH mixed solid was evaporated under 130° C. in a nitrogen atmosphere to obtain a white solid, and the white solid was used to catalytically synthesize an alkanolamide surfactant.

267 g of refined coconut oil with a saponification value of 251.6 mg KOH/g and 124 g of diethanol amine were added into a reactor with heating, condensing, reflux, temperature control and mixing functions and were evenly mixed, then 2.0 g of the NaOH and KOH compound catalyst was added to react for 4 h under 80° C. to obtain faint-yellow transparent liquid, and the liquid was layered after being cooled to a room temperature, wherein the conversion rate of the diethanol amine was 88.75%.

Figure 1:
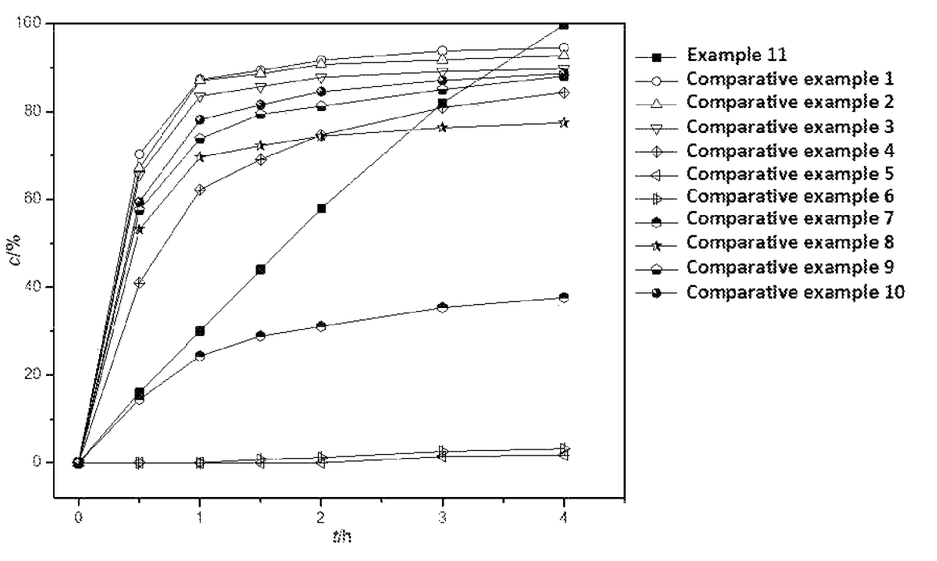

The relation of the conversion rate of the diethanol amine changing with time in Example 11 and the comparative examples 1-10 is shown in the provided FIGURE. It can be known from the FIGURE that although the conversion rates of the diethanol amine in Comparative examples 1 and 2 can reach 90%, the reaction rates are relatively high at the beginning, the activity of the catalysts is maintained for a short time, the products have relatively good quality and relatively dark color, the final yield is not higher than 95%, and the residual quantities of the alkanol amine in systems are high and both exceed 3%. In the present disclosure, the residual quantity of the alkanol amine=surplus of completely-reacted alkanol amine/total amount of the alkanol amine before reaction. The maintaining time of the activity of the catalysts in the comparative examples 3-10 is about 1 h, final reaction conversion rates are all relatively low, and the residual quantities of the alkanol amine are higher. The calcium-based catalyst obtained in Example 11 has a slow release feature, so that the catalyst still have relatively high catalytic reaction activity in the late reaction period, it is guaranteed that the alkanol amine is converted into the alkanolamide surfactant with a high conversion rate, the conversion rate of the alkanol amine is high, the residual quantity of the alkanol amine in the product is low, and the risk of nitrosamine caused by the residual alkanol amine in the product is greatly lowered. Meanwhile, the speed in the early reaction period is greatly reduced due to control of slow release of the catalyst, and a deepened color of the product caused by poor heat transfer in the synthesis process due to excessively fast reaction in the early period is effectively avoided.

What is claimed is:

1. A method for preparing an alkanolamide, comprising:
mixing simultaneously in parts by weight in water as a solvent: 1 to 20 parts of CaO and/or $Ca(OH)_2$, 20 to 500 parts of KOH, and 20 to 500 parts of NaOH, to form a calcium-based catalyst solution,
drying the calcium-based catalyst solution to dryness at a temperature between 80° C. and 280° C., thereby producing a solid calcium-based catalyst,
crushing the solid calcium-based catalyst,
catalyzing the amidation of an ester compound and alkanolamine by contacting the solid calcium-based catalyst with the ester compound and alkanolamine,
wherein the ester compound comprises an oil and/or a fatty acid ester,
wherein the oil is selected from one or more of coconut oil, palm kernel oil, palm oil, soybean oil, rapeseed oil, linseed oil, tall oil, lard oil, and tallow,
wherein the fatty acid ester is selected from one or more of methyl caprate, methyl laurate, methyl myristate, methyl palmitate, methyl stearate, methyl 9-hydroxystearate, methyl oleate, methyl linoleate, methyl erucate, ethyl caprate, ethyl laurate, ethyl myristate, ethyl palmitate, ethyl stearate, ethyl 9-hydroxystearate, ethyl oleate, ethyl linoleate, ethyl erucate, fatty acid ethyl esters obtained by hydrolytic esterification of the oil, and fatty acid methyl esters and/or fatty acid ethyl esters obtained by transesterification of fatty acids.

2. The method according to claim 1, wherein the alkanolamine is one or more of ethanol amine, diethanol amine, and methyl monoethanol amine.

3. The method according to claim 1, wherein when the ester compound is the oil, a ratio of the ester compound to the alkanolamine by weight is 1 to 1.05:3.

4. The method according to claim 1, wherein when the ester compound is the fatty acid ester, a ratio of the ester compound to the alkanolamine by weight is 1 to 1.05:1.

5. The method according to claim 1, wherein an addition amount of the calcium-based catalyst is 0.05 wt % to 2 wt % based on a total mass of the ester compound and the alkanolamine.

6. The method according to claim 2, wherein an addition amount of the calcium-based catalyst is 0.05 wt % to 2 wt % based on a total mass of the ester compound and the alkanolamine.

7. The method according to claim 3, wherein an addition amount of the calcium-based catalyst is 0.05 wt % to 2 wt % based on a total mass of the ester compound and the alkanolamine.

8. The method according to claim 4, wherein an addition amount of the calcium-based catalyst is 0.05 wt % to 2 wt % based on a total mass of the ester compound and the alkanolamine.

9. The method according to claim 1, wherein catalyzing the amidation of an ester compound and alkanolamine is conducted at a reaction temperature of 35° C. to 120° C.

10. The method according to claim 2, wherein catalyzing the amidation of an ester compound and alkanolamine is conducted at a reaction temperature of 35° C. to 120° C.

11. The method according to claim 3, wherein catalyzing the amidation of an ester compound and alkanolamine is conducted at a reaction temperature of 35° C. to 120° C.

12. The method according to claim 4, wherein catalyzing the amidation of an ester compound and alkanolamine is conducted at a reaction temperature of 35° C. to 120° C.

13. The method according to claim 1, further comprising dispersing CaO or $Ca(OH)_2$ in water to prepare a 1 wt % to 20 wt % $Ca(OH)_2$ solution, and then mixing the $Ca(OH)_2$ solution with the NaOH and KOH to prepare the calcium-based catalyst solution.

14. The method according to claim 1, further comprising dissolving KOH in water or diluting a KOH concentrated solution to prepare a 20 to 50 wt % KOH solution, and then mixing the 20 to 50 wt % KOH solution with the CaO and/or $Ca(OH)_2$, and NaOH, to produce the calcium-based catalyst solution.

15. The method according to claim 1, further comprising dissolving NaOH in water or diluting a NaOH concentrated solution to prepare a 20 wt % to 50 wt % NaOH solution, and then mixing the 20 wt % to 50 wt % NaOH solution with the CaO and/or $Ca(OH)_2$, and KOH, to prepare the calcium-based catalyst solution.

* * * * *